United States Patent [19]

Yamade et al.

[11] 4,125,611
[45] Nov. 14, 1978

[54] 3-HETEROCYCLIC THIOMETHYL 7-METHOXY-7 SUBSTITUTED ACETAMIDO CEPHALOSPORINS

[75] Inventors: Hirotada Yamade; Takenari Nakagome, both of Nishinomiya; Toshiaki Komatsu, Takarazuk, all of Japan

[73] Assignee: Sumitomo Chemical Company, Limited, Osaka, Japan

[21] Appl. No.: 745,749

[22] Filed: Nov. 29, 1976

[30] Foreign Application Priority Data

Nov. 28, 1975 [JP] Japan .................................. 50/142647

[51] Int. Cl.$^2$ .......................................... C07D 501/36
[52] U.S. Cl. ...................................... 424/246; 544/21
[58] Field of Search ....................... 260/243 C; 544/21; 424/246

[56] References Cited

U.S. PATENT DOCUMENTS

| | | | |
|---|---|---|---|
| 3,984,401 | 10/1976 | Terao et al. ............................. | 544/21 |
| 3,989,687 | 11/1976 | Bambury et al. .................. | 260/243 C |
| 4,041,161 | 8/1977 | Kocsis et al. ........................... | 544/22 |

Primary Examiner—Donald G. Daus
Assistant Examiner—David E. Wheeler
Attorney, Agent, or Firm—Sughrue, Rothwell, Mion, Zinn and Macpeak

[57] ABSTRACT

A cephalosporin of the formula (I):

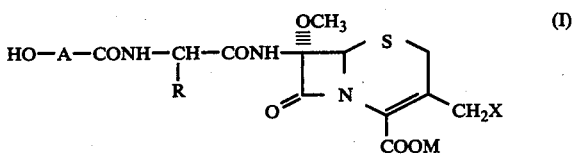

wherein A is a mono- or polycyclic heteroaromatic ring containing at least one nitrogen atom as a hetero atom, which may be unsubstituted or substituted; R is a phenyl group which may be unsubstituted or substituted, a thienyl group, a furyl group, a cyclohexadienyl group or a cyclohexenyl group; X is an acetoxy group, a pyridinium group which may be unsubstituted or substituted with a methyl or carbamoyl group, a group of the formula:

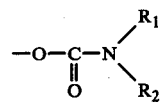

in which $R_1$ and $R_2$, which may be the same or different, each is a hydrogen atom or a $(C_1 - C_4)$ alkyl group, or a group of the formula:

-S-Het in which Het is a heterocyclic ring containing 1 to 5 oxygen, nitrogen and sulfur atoms as a hetero atom, in which the heterocyclic ring system may be either polycyclic or 5- or 6-membered monocyclic and may be unsubstituted or substituted; and M is a hydrogen atom or a biologically active carboxyl-protecting group, or is an anionic charge only when X is a pyridinium group; and the pharmaceutically acceptable salts thereof, which are useful as antimicrobial agents and prepared by the reaction of a compound of the formula (II):

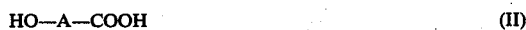

wherein A is as defined above, or a reactive derivative thereof, with a compound of the formula (III):

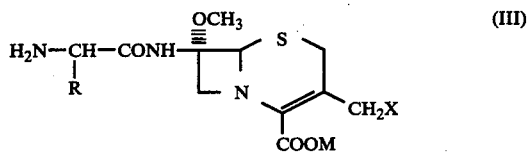

wherein R, M and X are as defined above, or a derivative thereof.

14 Claims, No Drawings

3-HETEROCYCLIC THIOMETHYL 7-METHOXY-7 SUBSTITUTED ACETAMIDO CEPHALOSPORINS

BACKGROUND OF THE INVENTION

1. Field of the Invention

The present invention relates to a novel antimicrobial agent for infectious diseases caused by Gram-negative as well as Gram-positive bacteria and to a process for the production of the same. More particularly, the invention pertains to a cephalosporin of the formula (I):

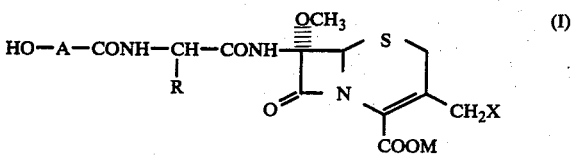

wherein A, R, M and X are as described hereinafter and pharmaceutically acceptable salts thereof and to process for the preparation thereof.

2. Description of the Prior Art

It is known that cephalosporin series compounds such as Cephalothin and Cefazolin are very effective and are widely used as chemotherapeutic agents for infectious diseases caused by Gram-positive or Gram-negative bacteria.

However, these cephalosporin series compounds have no effect on infectious diseases caused by *Pseudomonas aeruginosa* which have been increasingly spreading in recent years, and are often very difficult to cure. Cephalosporin series compounds which are effective against *Pseudomonas aeruginosa* are not yet commercially available.

SUMMARY OF THE INVENTION

In one embodiment, the present invention provides a cephalosporin of the formula (I):

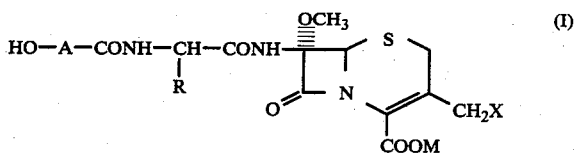

wherein A is a mono- or polycyclic heteroaromatic ring containing at least 1 nitrogen atom as a hetero atom, which may be unsubstituted or substituted with one or more substituents; R is a phenyl group which may be unsubstituted or substituted, a thienyl group, a furyl group, a cyclohexadienyl group or a cyclohexenyl group; X is an acetoxy group, a pyridinium group which may be unsubstituted or substituted with a methyl or carbamoyl group, a group of the formula:

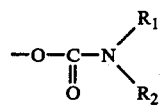

in which $R_1$ and $R_2$, which may be the same or different, each is a hydrogen atom or a ($C_1$ - $C_4$)alkyl group; or a group of the formula:

-S-Het in which Het is a heterocyclic ring containing 1 to 5 oxygen, nitrogen and sulfur atoms as hetero atoms, in which the ring system may be either polycyclic or 5- or 6-membered monocyclic and may be unsubstituted or substituted; and M is a hydrogen atom or a biologically active carboxyl-protective group, or is an anionic charge only when X is a pyridinium group; and the pharmaceutically acceptable salts thereof.

In another embodiment, the invention provides an antimicrobial composition containing a therapeutically effective amount of at least one compound of the formula (I) or a non-toxic pharmaceutically acceptable salt thereof (I) as an active ingredient.

In a further embodiment, the invention provides processes described hereinafter in detail for the preparation of the compounds of the formula (I) and the non-toxic pharmaceutically acceptable salts thereof.

In an even further embodiment, the invention provides a method of treating or preventing infectious diseases caused by Gram-positive or Gram-negative bacteria in an animal which comprises administering an antimicrobially effective amount of at least one compound of the formula (I) to the animal.

DETAILED DESCRIPTION OF THE INVENTION

As the result of various studies seeking a cephalosporin series compound having a strong anti-Pseudomonas activity and a broad antimicrobial spectral activity, it has been found that cephalosporins of the formula (I) as described above and the pharmaceutically acceptable salts thereof have a strong antimicrobial activity against Gram-positive as well as Gram-negative bacteria including *Pseudomonas aeruginosa* and are useful as antimicrobial agents for the treatment or the prevention of infectious diseases caused by Gram-negative or Gram-positive bacteria.

Particularly, the compounds of the invention exhibit a noticeable antimicrobial activity against bacteria to which known cephalosporin series compounds are barely effective, such as *Pseudomonas aeruginosa*, indole positive *Proteus, Serratia, Enterobacter aerogenus* and Cephaloridine resistant *E. coli*.

In the compound of the formula (I), the heteroaromatic ring represented by A may be, for example, quinoline, isoquinoline, cinnoline, naphthyridine, quinoxaline, pyrazolopyridine, pyridopyrazine, thiazolopyrimidine, pyridopyrimidine, pyrimidinopyridazine, thienopyridine, thiazolopyridine, pyridine, pyrimidine, pyridazine, triazine and pyrazine. These heteroaromatic rings for A may be substituted with 1 to 4 substituents, of which examples are halogen (e.g., fluorine, chlorine, bromine and iodine) atoms, lower alkyl, lower alkoxy, lower alkanoyl, lower alkoxycarbonyl, lower alkylthio, mercapto, hydroxy, lower alkoxymethyl, cyano, nitro, lower alkylsulfonyl, arylsulfonyl, sulfamoyl, carbamoyl, aryloxycarbonylamino, acetoacetylamino, lower alkylamino, lower dialkylamino, lower haloalkyl, lower alkenyl, aryl, cycloalkyl and cycloalkylene groups, and heterocyclic ring groups containing 1 or 2 nitrogen atoms.

In the above groups, the terms "lower alkyl" preferably includes an alkyl having up to 4 carbon atoms; "lower alkoxy" preferably includes an alkoxy having up to 4 carbon atoms; "lower alkanoyl" preferably includes an alkanoyl having up to 5 carbon atoms; "lower alkoxycarbonyl" preferably includes an alkoxycarbonyl having up to 5 carbon atoms; "lower alkylthio" preferably includes an alkylthio having up to 4 carbon atoms; "lower alkoxymethyl" preferably includes an alkoxymethyl having up to 5 carbon atoms; "lower alkylsulfonyl" preferably includes an alkylsulfonyl having up to 4 carbon atoms; "arylsulfonyl" preferably includes a phenylsulfonyl; "aryloxycarbonylamino" preferably includes a phenyloxycarbonylamino; "lower alkylamino" preferably includes an alkylamino having up to 4 carbon atoms; "lower dialkylamino" preferably includes a dialkylamino of which each of the alkyl moieties thereof has up to 4 carbon atoms; "lower haloalkyl" preferably includes a chloro- or fluoro-substituted alkyl having up to 4 carbon atoms, for example, chloromethyl, trifluoromethyl, 2,2,2-trichloroethyl; "lower alkenyl" preferably includes an alkenyl having up to 4 carbon atoms; "aryl" preferably includes phenyl; "cycloalkyl" preferably includes a cycloalkyl having 3 to 6 carbon atoms; "cycloalkylene" preferably includes a cycloalkylene having 4 to 6 carbon atoms; and "heterocyclic ring containing 1 or 2 nitrogen atoms" preferably includes pyrrolidinyl, morpholyl, piperazinyl or piperidinyl.

In the compound of the formula (I), R represents a phenyl group which may be unsubstituted or substituted, a thienyl, furyl, cyclohexadienyl or cyclohexenyl group and the term "a phenyl group" which may be substituted as used with respect to R includes an optionally substituted phenyl group of the formula:

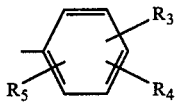

wherein $R_3$, $R_4$ and $R_5$, which may be the same or different, each represents hydrogen, nitro, lower dialkylamino (preferably, di($C_1$ - $C_4$)alkylamino), lower alkanoylamino (preferably, ($C_2$ - $C_5$)alkanoylamino), lower alkylsulfonamido (preferably, ($C_1$ - $C_4$)alkylsulfonamido), amino, hydroxy, lower alkanoyloxy (preferably, ($C_2$ - $C_5$)alkanoyloxy), lower alkyl (preferably, ($C_1$ - $C_4$)alkyl), lower alkoxy (preferably, ($C_1$ - $C_4$)alkoxy), chloro, bromo, fluoro, iodo, trifluoromethyl, hydroxymethyl, ureido or sulfamyl, preferably hydrogen, hydroxy, chlorine, fluorine or methoxy.

The heterocyclic ring represented by the symbol Het in the -S-Het group may be unsubstituted or substituted with one or two of ($C_1$ - $C_4$)alkyl, ($C_1$ - $C_4$)alkoxy, hydroxy, mercapto, hydroxymethyl, aminomethyl, or methylamino.

Examples of suitable heterocyclic rings are tetrazolyl, thiadiazolyl, triazolyl, oxadiazolyl, pyridazinyl, tetrazolo[4,5-b]pyridazinyl, pyridazino[3,2-c]-S-triazolyl, or pyridazino[2,1-c]-S-triazolyl, and particularly preferred are 1-methyl-tetrazol-5-yl, 2-methyl-1,3,4-thiadiazol-5-yl, 1,2,3-triazol-5-yl, 1,2,4-triazol-3-yl, tetrazol-5-yl, 2-methyltetrazol-5-yl, 2-mercapto-1,3,4-thiadiazol-5-yl, 2-hydroxymethyl-1,3,4-oxadiazol-5-yl, 2-hydroxymethyl-1,3,4-thiadiazol-5-yl, 2-aminomethyl-1,3,4-thiadiazol-5-yl, 3-hydroxypyridazin-6-yl, 1,3,4-thiadiazol-5-yl, 2-methylamino-1,3,4-thiadiazol-5-yl, 2-oxo-1,3,4-thiadiazol-5-yl, 1-ethyltetrazol-5-yl, 1-phenyltetrazol-5-yl, tetrazol[4,5-b]pyridazin-6-yl, 3-hydroxypyridazino[3,2-c]-S-triazol-6-yl, pyrido[2,1-c]-S-triazol-3-yl, and pyridazino[2,1-c]-S-triazol-3-yl.

With respect to X in the formula (I) above, the term "a pyridinium group which may be substituted with a methyl or carbamoyl group" may be represented by the formula:

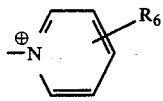

wherein $R_6$ is a hydrogen atom, a methyl group or a carbamoyl group.

In the formula (I) above, M represents a hydrogen atom or a biologically active carboxyl-protecting group and M also can be an anionic charge when X is pyridinium, that is,

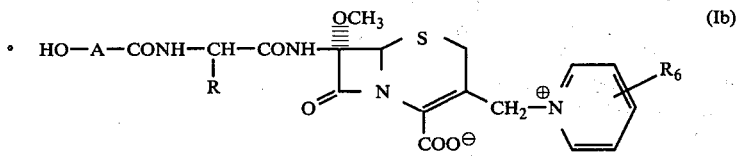

(Ib)

The term "biologically active carboxyl-protecting group" as used above means a pharmaceutically acceptable carboxyl-protecting group which is split off to give the carboxyl group when metabolized into a living organism, of which examples are a phenacyl, lower acyloxymethyl (preferably, ($C_3$ - $C_8$)acyloxymethyl), benzoyloxymethyl, phthalidyl and indanyl group.

Examples of non-toxic pharmaceutically acceptable salts derived from the compounds of formula (I) include the sodium salt, the potassium salt, the calcium salt, the magnesium salt, the triethylamine salt, the diethanolamine salt, the morpholine salt, the procaine salt, the L-arginine salt, and the L-lysine salt.

The α-carbon atom of the side chain (phenylglycine moiety) attached to the 7-position of the formula (I) is an asymmetric carbon atom and therefore two optically active isomers exist. These two isomers (D-diastereomer and L-diastereomer) and the DL-form are included within the scope of the present invention, but the D-diastereomer is preferred.

In the formula (I), the hydroxy group on the heteroaromatic ring A is preferably linked to a carbon atom adjacent the carbon atom to which the

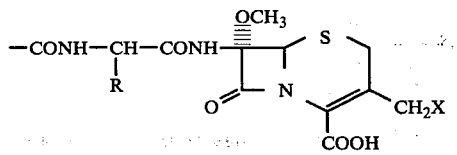

moiety is connected.

Among the cephalosporins of the formula (I), the following compounds are preferred:

Compounds of the formula (I), wherein R is

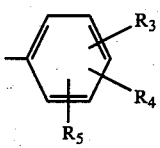

(in which $R_3$, $R_4$ and $R_5$ are each hydrogen, hydroxy, ($C_1$ - $C_4$)alkoxy or chlorine), X is —OCONH$_2$ or -S-Het (wherein Het is tetrazole, thiadiazole, triazole or tetrazolopyridazine, each of which may be unsubstituted or substituted with one substituent selected from the group consisting of ($C_1$ - $C_4$)alkyl, hydroxy, hydroxymethyl, mercapto, aminomethyl and methylamino), A is naphthyridine, pyridopyrazine, pyridopyrimidine or pyridinium, each of which may be unsubstituted or substituted with one substituent selected from the group consisting of ($C_1$ - $C_4$)alkyl, ($C_1$ - $C_4$)alkoxy, ($C_1$ - $C_4$)alkylmercapto, di-($C_1$ - $C_4$)alkylamino, hydroxy and piperazinyl, and M is hydrogen, and their non-toxic, pharmaceutically acceptable salts;

Compounds of the formula (I), wherein R is phenyl, X is —OCOCH$_3$, A is naphthyridine which may be unsubstituted or substituted with one substituent selected from the group consisting of ($C_1$ - $C_4$)alkyl, ($C_1$ - $C_4$)alkoxy and di-($C_1$ - $C_4$)alkylamino, and M is hydrogen, and their non-toxic, pharmaceutically acceptable salts;

Compounds of the formula (I), wherein R is phenyl, X is —OCOCH$_3$, A is pyridine which may be unsubstituted or substituted with ($C_1$ - $C_4$)alkyl or hydroxy, and M is hydrogen, and their non-toxic, pharmaceutically acceptable salts;

Compounds of the formula (I), wherein R is phenyl, X is —OCOCH$_3$, A is triazine substituted with hydroxy, and M is hydrogen, and their non-toxic, pharmaceutically acceptable salts;

Compounds of the formula (I), wherein R is phenyl, X is pyridinium which may be unsubstituted or substituted with carbamoyl, A is naphthyridine which may be unsubstituted or substituted with one substituent selected from the group consisting of ($C_1$ - $C_4$)alkyl, ($C_1$ - $C_4$)alkoxy and di-($C_1$ - $C_4$)alkylamino, and M is an anionic charge, and their non-toxic, pharmaceutically acceptable salts;

Compounds of the formula (I), wherein R is phenyl, X is pyridinium which may be unsubstituted or substituted with carbamoyl, A is pyridine which may be unsubstituted or substituted with ($C_1$ - $C_4$)alkyl or hydroxy, and M is an anionic charge, and their non-toxic, pharmaceutically acceptable salts;

Compounds of the formula (I), wherein R is phenyl, X is —OCONH$_2$, A is pyrimidine which may be unsubstituted or substituted with one substituent selected from the group consisting of hydroxy, mercapto and ($C_1$ - $C_4$)alkylmercapto, and M is hydrogen, and their non-toxic, pharmaceutically acceptable salts;

Compounds of the formula (I), wherein R is phenyl, X is —OCONH$_2$, A is triazine substituted with hydroxy, and M is hydrogen, and their non-toxic, pharmaceutically acceptable salts;

Compounds of the formula (I), wherein R is phenyl, X is -S-Het (in which Het is tetrazole or thiadiazole, each of which may be unsubstituted or substituted with ($C_1$ - $C_4$)alkyl), A is pyridopyrimidine which may be unsubstituted or substituted with ($C_1$ - $C_4$)alkylmercapto, or triazine substituted with hydroxy, and M is hydrogen, and their non-toxic, pharmaceutically acceptable salts;

Compounds of the formula (I), wherein R is

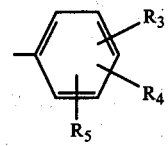

(in which $R_3$, $R_4$ and $R_5$ each is hydrogen or hydroxy), X is —OCOCH$_3$, A is naphthyridine which may be unsubstituted or substituted with one substituent selected from the group consisting of ($C_1$ - $C_4$)alkyl, ($C_1$ - $C_4$)alkoxy and di-($C_1$ - $C_4$)alkylamino, and M is hydrogen, and their non-toxic, pharmaceutically acceptable salts;

Compounds of the formula (I), wherein R is

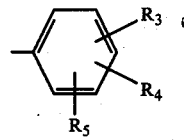

(in which $R_3$, $R_4$ and $R_5$ each is hydrogen or hydroxy), X is pyridinium substituted with carbamoyl, A is pyridopyrimidine which may be unsubstituted or substituted with ($C_1$ - $C_4$)alkylmercapto, and M is an anionic charge, and their non-toxic, pharmaceutically acceptable salts;

Compounds of the formula (I), wherein R is

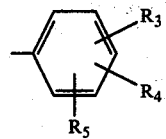

(in which $R_3$, $R_4$ and $R_5$ each is hydrogen, hydroxy or ($C_1$ - $C_4$)alkoxy), X is —OCONH$_2$, A is naphthyridine which may be unsubstituted or substituted with one substituent selected from the group consisting of ($C_1$ - $C_4$)alkyl, ($C_1$ - $C_4$)alkoxy and di($C_1$ - $C_4$)alkylamino, and M is hydrogen, and their non-toxic, pharmaceutically acceptable salts;

Compounds of the formula (I), wherein R is

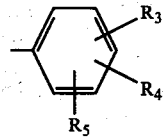

(in which $R_3$, $R_4$ and $R_5$ each is hydrogen, hydroxy or ($C_1$ - $C_4$)alkoxy), X is —OCONH$_2$, A is pyridopyrimidine which may be unsubstituted or substituted with ($C_1$ - $C_4$)alkylmercapto or piperazyl, and M is hydrogen, and their non-toxic, pharmaceutically acceptable salts;

Compounds of the formula (I), wherein R is

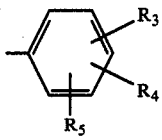

(in which R$_3$, R$_4$ and R$_5$ each is hydrogen, hydroxy or (C$_1$ - C$_4$)alkoxy), X is —OCONH$_2$, A is pyridine which may be unsubstituted or substituted with (C$_1$ - C$_4$)alkyl or hydroxy, and M is hydrogen, and their non-toxic, pharmaceutically acceptable salts;

Compounds of the formula (I), wherein R is

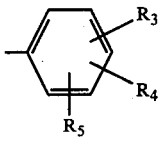

(in which R$_3$, R$_4$ and R$_5$ each is hydrogen, hydroxy or (C$_1$ - C$_4$)alkoxy), X is —OCONH$_2$, A is thiazolopyridine, and M is hydrogen, and their non-toxic, pharmaceutically acceptable salts;

Compounds of the formula (I), wherein R is

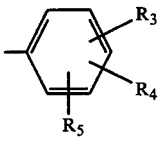

(in which R$_3$, R$_4$ and R$_5$ each is hydrogen, hydroxy or (C$_1$ - C$_4$)alkoxy), X is —OCONH$_2$, A is triazine substituted with hydroxy, and M is hydrogen, and their non-toxic, pharmaceutically acceptable salts;

Compounds of the formula (I), wherein R is

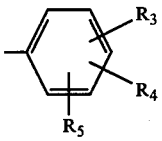

(in which R$_3$, R$_4$ and R$_5$ each is hydrogen, hydroxy, (C$_1$ - C$_4$)alkoxy, chlorine, or fluorine), X is -S-Het wherein Het is tetrazole, triazole, thiadiazole, pyridazine or tetrazolopyridazine, each of which may be unsubstituted or substituted with one substituent selected from the group consisting of (C$_1$ - C$_4$)alkyl, hydroxy, hydroxymethyl, mercapto, methylamino and aminomethyl, A is naphthyridine, pyridopyrazine, pyrazolopyridine, pyridopyrimidine, thienopyridine, pyridine, pyrimidine, pyridazine, pyrazine or triazine, each of which may be unsubstituted or substituted with one substituent selected from the group consisting of (C$_1$ - C$_4$)alkyl, (C$_1$ - C$_4$)alkoxy, (C$_1$ - C$_4$)alkylmercapto, di-(C$_1$ - C$_4$)alkylamino and hydroxy, and M is hydrogen, and their non-toxic, pharmaceutically acceptable salts;

Compounds of the formula (I), wherein R is thienyl, X is —OCONH$_2$, A is naphthyridine which may be unsubstituted or substituted with one substituent selected from the group consisting of (C$_1$ - C$_4$)alkyl, (C$_1$ - C$_4$)alkoxy, (C$_1$ - C$_4$)alkylmercapto and di-(C$_1$ - C$_4$)alkylamino, and M is hydrogen, and their non-toxic, pharmaceutically acceptable salts;

Compounds of the formula (I), wherein R is thienyl, X is -S-Het wherein Het is tetrazole which may be unsubstituted or substituted with (C$_1$ - C$_4$)alkyl, A is pyridine which may be unsubstituted or substituted with (C$_1$ - C$_4$)alkyl or hydroxy, and M is hydrogen, and their non-toxic, pharmaceutically acceptable salts;

Compounds of the formula (I), wherein R is cyclohexadienyl, X is -S-Het wherein Het is thiadiazole which may be unsubstituted or substituted with (C$_1$ - C$_4$)alkyl, A is naphthyridine which may be unsubstituted or substituted with one substituent selected from the group consisting of (C$_1$ - C$_4$)alkyl, (C$_1$ - C$_4$)alkoxy, (C$_1$ - C$_4$)alkylmercapto and di-(C$_1$ - C$_4$)alkylamino, and M is hydrogen, and their non-toxic, pharmaceutically acceptable salts;

Compounds of the formula (I), wherein R is cyclohexadienyl, X is —OCONH$_2$, A is pyridine which may be unsubstituted or substituted with (C$_1$ - C$_4$)alkyl or hydroxy, and M is hydrogen, and their non-toxic, pharmaceutically acceptable salts;

Compounds of the formula (I), wherein R is furyl, X is -S-Het wherein Het is tetrazole which may be unsubstituted or substituted with (C$_1$ - C$_4$)alkyl, A is naphthyridine which may be unsubstituted or substituted with one substituent selected from the group consisting of (C$_1$ - C$_4$)alkyl, (C$_1$ - C$_4$)alkoxy, (C$_1$ - C$_4$)alkylmercapto and di-(C$_1$ - C$_4$)alkylamino, and M is hydrogen, and their non-toxic, pharmaceutically acceptable salts;

Compounds of the formula (I), wherein R is cyclohexenyl, X is —OCOCH$_3$, A is naphthyridine which may be unsubstituted or substituted with one substituent selected from the group consisting of (C$_1$ - C$_4$)alkyl, (C$_1$ - C$_4$)alkoxy, (C$_1$ - C$_4$)alkylmercapto and di-(C$_1$ - C$_4$)alkylamino, and M is hydrogen, and their non-toxic, pharmaceutically acceptable salts;

Compounds of the formula (I), wherein R is phenyl, X is —OCONH$_2$, A is pyridine which may be unsubstituted or substituted with (C$_1$ - C$_4$)alkyl or hydroxy, and M is hydrogen, and their non-toxic, pharmaceutically acceptable salts;

Compounds of the formula (I), wherein R is phenyl, X is —OCONH$_2$, A is naphthyridine which may be unsubstituted or substituted with one substituent selected from the group consisting of (C$_1$ - C$_4$)alkyl, (C$_1$ - C$_4$)alkoxy, (C$_1$ - C$_4$)alkylmercapto and di-(C$_1$ - C$_4$)alkylamino, and M is hydrogen, and their non-toxic, pharmaceutically acceptable salts;

Compounds of the formula (I), wherein R is phenyl, X is -S-Het in which Het is tetrazole or thiadiazole, each of which may be unsubstituted or substituted with (C$_1$ - C$_4$)alkyl, A is pyridine or naphthyridine, each of which may be unsubstituted or substituted with one substituent selected from the group consisting of (C$_1$ - C$_4$)alkyl, (C$_1$ - C$_4$)alkoxy, (C$_1$ - C$_4$)alkylmercapto, di-(C$_1$ - C$_4$)alkylamino and hydroxy, and M is hydrogen, and their non-toxic, pharmaceutically acceptable salts;

Compounds of the formula (I), wherein R is

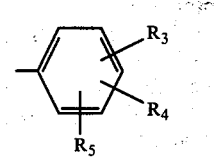

(in which $R_3$, $R_4$ and $R_5$ each is hydrogen or hydroxy), X is —OCOCH$_3$, A is pyridine which may be unsubstituted or substituted with ($C_1$ - $C_4$)alkyl or hydroxy, and M is hydrogen, and their non-toxic, pharmaceutically acceptable salts;

Compounds of the formula (I), wherein R is thienyl, X is —OCONH$_2$, A is pyridine which may be unsubstituted or substituted with ($C_1$ - $C_4$)alkyl or hydroxy, and M is hydrogen, and their non-toxic, pharmaceutically acceptable salts;

Compounds of the formula (I), wherein R is thienyl, X is -S-Het wherein Het is tetrazole or thiadiazole, each of which may be unsubstituted or substituted with ($C_1$ - $C_4$)alkyl, A is naphthyridine which may be unsubstituted or substituted with one substituent selected from the group consisting of ($C_1$ - $C_4$)alkyl, ($C_1$ - $C_4$)alkoxy, ($C_1$ - $C_4$)alkylmercapto and di-($C_1$ - $C_4$)alkylamino, and M is hydrogen, and their non-toxic, pharmaceutically acceptable salts;

Compounds of the formula (I), wherein R is cyclohexadienyl, X is -S-Het wherein Het is tetrazole or thiadiazole, each of which may be unsubstituted or substituted with ($C_1$ - $C_4$)alkyl, A is pyridine which may be unsubstituted or substituted with ($C_1$ - $C_4$)alkyl or hydroxy, and M is hydrogen, and their non-toxic, pharmaceutically acceptable salts;

Compounds of the formula (I), wherein R is cyclohexadienyl, X is —OCONH$_2$, A is naphthyridine which may be unsubstituted or substituted with one substituent selected from the group consisting of ($C_1$ - $C_4$)alkyl, ($C_1$ - $C_4$)alkoxy, ($C_1$ - $C_4$)alkylmercapto and di-($C_1$ - $C_4$)alkylamino, and M is hydrogen, and their non-toxic, pharmaceutically acceptable salts; and Compounds of the formula (I), wherein R is furyl, X is -S-Het wherein Het is tetrazole or thiadiazole, each of which may be unsubstituted or substituted with ($C_1$ - $C_4$)alkyl, A is pyridine which may be unsubstituted or substituted with ($C_1$ - $C_4$)alkyl or hydroxy, and M is hydrogen, and their non-toxic, pharmaceutically acceptable salts.

The compounds of the formula (I) of the present invention can be prepared by the following methods:

Method A

The compounds of the formula (I) above can be prepared by reacting a carboxylic acid of the formula (II):

HO—A—COOH    (II)

wherein A is as defined above, or a reactive derivative thereof, with a compound of the formula (III):

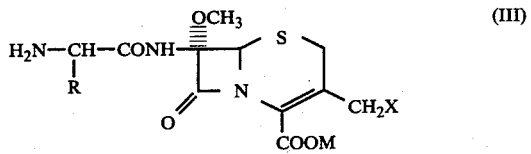

(III)

wherein R, M and X are as defined above, or a salt or derivative thereof.

Referring more particularly to this process, inert solvents which can be used in the reaction between the compounds of the formulas (II) and (III) include polar solvents such as dichloromethane, chloroform, acetone, tetrahydrofuran, dioxane, acetonitrile, methyl isobutyl ketone, ethyl alcohol, dimethylformamide, dimethylacetamide, dimethyl sulfoxide, nitromethane, hexamethylphosphoric triamide, sulfolane, and the like; non-polar solvents such as benzene, toluene, petroleum ether, n-hexane and the like; and a mixture thereof. These solvents can be used in combination with water.

The reactive derivatives of the compound (II) mean reactive derivatives of a carboxyl group, for example, an acid halide, an acid anhydride, an acid azolide, an active ester, an acid azide and the like. Referring more particularly to these reactive derivatives, examples include mixed acid anhydrides or symmetric acid anhydrides with acids such as dialkyl phosphoric acids, phenyl phosphoric acid, diphenyl phosphoric acid, dibenzyl phosphoric acid, halogenated phosphoric acids, dialkyl phosphorous acids, sulfuric acid, methanesulfonic acid, toluenesulfonic acid, naphthalenesulfonic acid, alkylcarbonates, aliphatic carboxylic acids (for example, pivalic acid, pentanoic acid, isopentanoic acid, 2-ethylbutanoic acid); acid azolides with imidazole, substituted imidazoles, dimethylpyrazole, triazole, tetrazole, and the like; and active esters such as cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenylthiophenyl ester, p-nitrophenylthio ester, p-cresolthio ester, carboxymethylthio ester, pyranyl ester, pyridyl ester, piperidyl ester, 8-quinolylthio ester, and esters with N,N'-dimethylhydroxylamine, 1-hydroxy-2-(1H)-pyridone, N-hydroxysuccinimide or N-hydroxyphthalimide.

Further, when the compounds of the formula (II) are used in the form of the free acid (or the salt thereof), it is preferred to carry out the reaction in the presence of coupling agents such as N,N'-dicyclohexylcarbodiimide, N-cyclohexyl-N-morpholinoethylcarbodiimide, N-cyclohexyl-N-(4-diethylaminocyclohexyl)carbodiimide, N,N'-diethylcarbodiimide, N,N'-diisopropylcarbodiimide, N-ethyl-N-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylenes, 1-alkoxy-1-chloroethylenes, trialkyl phosphites, polyphosphoric acid ethyl ester, polyphosphoric acid isopropyl ester, phosphorus oxychloride, oxalylchloride, triphenylphosphine, 2-ethyl-7-hydroxybenzisoxazolium salts,2-ethyl-5-(m-sulfonyl)isoxazolium hydroxide inner salts, (chloromethylene)dimethyl ammonium chloride and the like.

As described above, those amidating agents which are generally used in the fields of peptide chemistry, penicillin chemistry and cephalosporin chemistry can be used in the present invention.

Examples of salts of compounds of the formula (III) include an alkali metal salt or an alkaline earth metal salt (for example, the sodium, potassium, calcium, etc., salts) of acids of the formula (III); organic amine salts (for example, trimethylamine, triethylamine, quinoline, collidine, etc., salts) of the acids of the formula (III); and organic sulfonic acid salts (for example, toluenesulfonic acid, naphthalenesulfonic acid, tetralinsulfonic acid, trifluoroacetic acid, hydrochloric acid, etc., salts) of the acids of the formula (III).

The derivatives of the compounds of the formula (III) can be carboxyl-protected derivatives in which the carboxyl group is protected with a conventional protecting group including the above-described biologically active carboxyl-protecting group and such derivatives may be in the form of the ester, amide or anhydride thereof.

Examples of these carboxyl-protected derivatives include a silyl ester, an organo-tin ester, a toluenesulfonyl ethyl ester, a p-nitrobenzyl ester, a benzyl ester, a phenacyl ester, a 2-furylmethyl ester, a diphenylmethyl ester, a substituted diphenylmethyl ester, a p-methoxybenzyl ester, a trityl ester, a benzoyloxymethyl ester, a lower alkanoyl oxymethyl ester, a dimethylmethyleneamino ester, a p-nitrophenyl ester, a methylsulfonylphenyl ester, a methylthiophenyl ester, a t-butyl ester, a 4-picolyl ester, an iodoethyl ester, a trichloroethyl ester, a phthalimidomethyl ester, a 3,4-dimethoxy or 3,5-dimethylbenzyl ester, a 2-nitrobenzyl ester, a 2,2'-dinitrobenzyl ester, an acetyloxycarbonyl group, or a trichloroethyl ester thereof, and the compounds of the formula (III) in which the carboxyl group is protected with a group of the formula

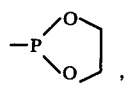

a group of the formula —N=CH—R' (in which R' is an alkyl or aryl group), or a group of the formula

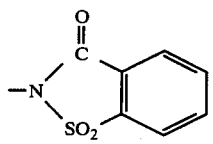

In case of the silyl ester, other substituents of the compound of the formula (III), if any, such as a hydroxy group or an amino group may be silylated.

In case of these derivatives of compounds of the formula (III), their hydrochloric acid, p-toluenesulfonic acid, naphthalene sulfonic acid or tetralin sulfonic acid salts may also be used.

The carboxyl-protecting group can be removed after the reaction under mild conditions, if necessary. For example, they can be removed by a solvolysis such as a hydrolysis and an alcoholysis, a catalytic hydrogenation, a reduction, an oxidation, a nucleophilic substitution reaction, a photochemical reaction or an enzymatic reaction.

The reaction between the acid of the formula (II) or the reactive derivative thereof and the compound of the formula (III) or the derivative thereof can generally be carried out at a temperature ranging from about −50° C. to about 50° C.

Method B

The compounds of the formula (Ia):

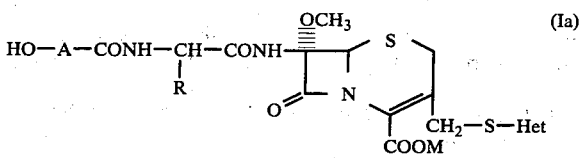

wherein A, R, Het and M are as defined above, can also be prepared by reacting a compound of the formula (IV):

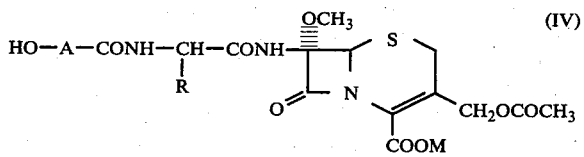

wherein A, R and M are each as defined above, with a thiol represented by the formula (V):

HS-Het (V)

wherein Het is as defined above.

Various well-known methods (as described in Japanese Patent Publication Nos. 12136/1971, 2340/1971, 14734/1971, Japanese Patent Application (OPI) No. 68593/1973 and Journal of the Chemical Society, 1965, 5015) can be employed in the above reaction. For example, the reaction can be carried out in an inert solvent such as water, acetone, dimethylformamide, dimethylsulfoxide, methanol, ethanol, dioxane, tetrahydrofuran, sulfolane, and the like. These organic solvents may be used in combination with water and a suitable buffer may also be used. It is advantageous to carry out the reaction under neutral or wealky alkaline conditions. When the compounds of the formula (IV) are used in the form of the free carboxylic acid, the reaction preferably is carried out in the presence of a base such as sodium bicarbonate or triethylamine. In general, the reaction is preferably conducted at about 50° C. to about 60° C.

Method C

The compounds of the formula (Ib):

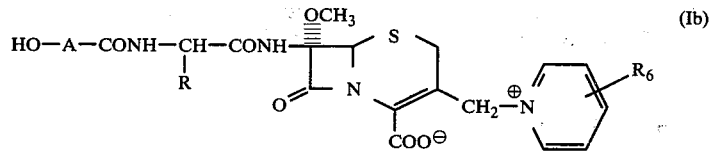

wherein A, R and R₆ are as defined above, may also be prepared by reacting a compound of the formula (IV):

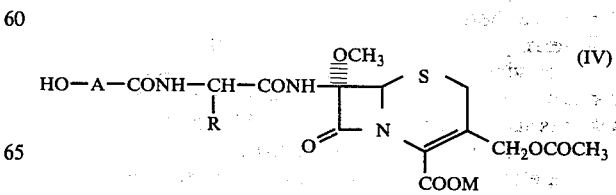

with a compound of the formula (VI):

 (VI)

wherein $R_6$ is as defined above. This preparation can be carried out using known methods as described in U.S. Pat. No. 3,225,038; *Journal of Organic Chemistry*, Vol. 32, 500 (1967); and *Journal of Medicinal Chemistry*, Vol. 17, 1312–1315. The reaction is usually carried out in the presence of water. However, it can also be carried out using the compound of the formula (VI) per se as a solvent. The reaction is preferably carried out at about 40° C. to about 60° C. It is advantageous to carry out the reaction in the presence of an inorganic salt such as potassium thiocyanate or potassium iodide.

Method D

Further, another method of the preparation of the compounds of the formula (I) is a method which comprises reacting an acylamino carboxylic acid of the formula (VII):

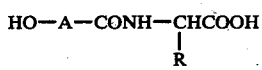 (VII)

wherein A and R are each as defined above, or a reactive derivative thereof with a compound of the formula (VIII):

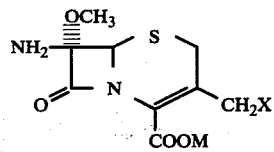 (VIII)

wherein X and M are as defined above, or a derivative thereof, and when X is an —OCOCH₃ group, further reacting the resulting reaction product, if necessary, with a heterocyclic thiol of the formula (V):

Hs-Het (V)

in which Het is as defined above, or a compound of the formula (VI):

 (VI)

wherein $R_6$ is as defined above. This method can be carried out in a similar manner as the reaction between the compound of the formula (II) and the compound of the formula (III).

Method E

Further, the compound of the formula (I) also can be prepared from a compound of the formula (IX):

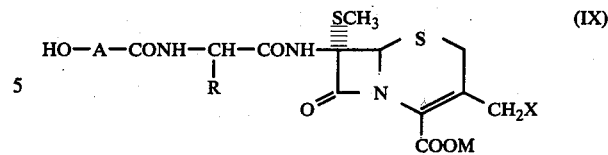 (IX)

wherein A, R, M and X are as defined above, by applying known methods as disclosed, for example, in *Journal of Organic Chemistry*, Vol. 38, 943, and Japanese Patent Application (OPI) Nos. 52084/1975 and 125390/1974.

Method F

Further, another method of preparation of the compound of the formula (I) is a method which comprises reacting a compound of the formula (VII):

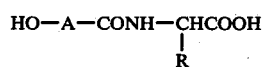 (VII)

wherein A and R are each as defined above, or a reactive derivative thereof, with a compound of the formula (X):

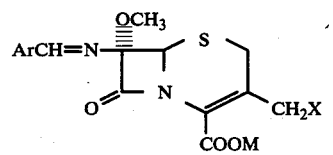 (X)

wherein Ar is phenyl, p-nitrophenyl, or 3,5-di-t-butyl-4-hydroxyphenyl, and M and X are as defined above, or a derivative thereof.

Method G

Further, another method of preparation of the compound of the formula (I) is a method which comprises reacting a compound of the formula (VII):

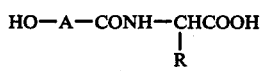 (VII)

wherein A and R are each as defined above, or a reactive derivative thereof, with a compound of the formula (XI):

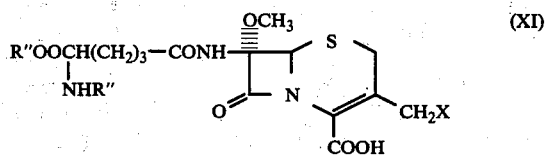 (XI)

wherein R" is hydrogen or an easily removable protective group, and X is as defined above.

Method H

Further, the compound of the formula (I) can be prepared from a compound of the formula (XII):

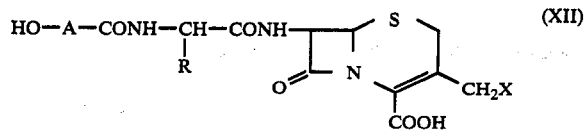

(XII)

wherein A, R, and X are as defined above, by applying known methods as disclosed, for example, in *Journal of the American Chemical Society*, Vol. 95, 2403, (1973), Japanese Patent Application (OPI) No. 85595/1973, and *Journal of Organic Chemistry*, Vol. 38, 1436 (1973).

The compound of the formula (III), and a salt and derivative thereof may be prepared using a known process. For example, 3-acetoxymethyl-7α-methoxy-7β-2-amino-2-phenylacetamido-3-cephem-4-carboxylic acid, 3-methyl-7-methoxy-7-(2-amino-2-phenylacetamido)-3-cephem-4-carboxylic acid, and 3-carbamoyloxymethyl-7α-methoxy-7β-[2-amino-2-(2-thienyl)acetamido]-3-cephem-4-carboxylic acid and the diphenylmethyl ester thereof, respectively, are prepared by known methods as disclosed in Japanese Patent Application (OPI) Nos. 931/1972, 85595/1973 and 67293/1973.

The compounds of the formula (I) of this invention are valuable as antibacterial agents, nutritional supplements in animal feeds, therapeutic agents for poultry and animals, including man, and are especially useful in the treatment of infectious diseases caused by Gram-positive bacteria such as *Staphylococcus auerus*, *Staphylococcus epidermidis*, *Staphylococcus pyogenes*, *Diplococcus pneumoniae*, *Sarcina lutea*, *Bacillus subtilis*, *Clostridium perfringens* and *Corynebacterium diphtheriae*, and Gram-negative bacteria such as *Escherichia coli*, *Neisseria gonouhoeae*, *Salmonella typhi*, *Klebsiella pneumoniae*, *Shigella dysenteriae*, *Shigella flexneri*, *Shigella sonnei*, *Enterobacter aerogenes*, *Proteus mirabilis*, *Proteus vulgaris*, *Pseudomonas aeruginosa* and *Serratia marcescens*. For the treatment or prevention of such infectious diseases, the compounds of this invention, either individually or in combination with a pharmaceutically acceptable carrier or diluent, or another active ingredient(s), e.g., another chemotherapeutic agent(s), can be administered intramuscularly or intravenously to a subject.

The dosage of the compounds of the formula (I) of this invention will vary with the body weight, age and conditions of an individual subject, the kind of bacteria, and the pharmacokinetic properties of the particular compound chosen. Although the particular dosage will be determined by a physician taking these factors into consideration, the compounds of the formula (I) are, in general, most desirably administered intramuscularly or intravenously at a dosage ranging from about 2 mg/kg of body weight/day to 400 mg/kg of body weight/day, preferably from 8 mg/kg of body weight/day to 120 mg/kg of body weight/day in a single dose or in multiple doses 1 to 5 times daily.

For intramuscular or intravenous administrations the compounds of this invention may be used in the form of sterile solution or suspension containing additionally a pharmaceutically acceptable diluent or carrier such as water, saline solution, Ringer's solution, glycerin, polyethylene glycol, etc. These preparations or formulations may also contain suitable auxiliary materials, such as stabilizers, buffer substances, wetting agents, emulsifiers, local anesthetics, or salts that regulate the osmotic pressure. The compounds of the formula (I) of this invention may also be applied topically in the form of an ointment or cream to the skin or other organs as a sterilizer or disinfectant.

The present invention is further illustrated in greater detail by the following examples, but the invention is not to be construed as being limited by these examples. Unless otherwise indicated, all parts, percents and ratios are by weight.

EXAMPLE 1

Preparation of 3-Acetoxymethyl-7α-methoxy-7β-[D-2-(4-hydroxy-1,5-naphthyridine-3-carbonamido)-2-phenylacetamido]-3-cephem-4-carboxylic Acid

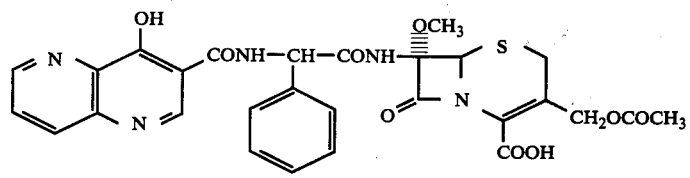

0.549 g of the trifluoroacetate salt of 3-acetoxymethyl-7α-methoxy-7β-[(D-2-phenyl)acetamido]-3-cephem-4-carboxylic acid was dissolved in 5 ml of dimethyl sulfoxide, and 0.303 g of triethylamine was then added to the solution. Then, 0.287 g of 4-hydroxy-1,5-naphthyridine-3-carboxylic acid N-hydroxysuccinimide ester was added to the solution, and the mixture was allowed to react for 1 hour at room temperature while stirring. After removal of any insoluble substances by filtration, 0.332 g of sodium 2-ethylhexanoate was added to the filtrate, and the resulting solution was added to 150 ml of acetone. The crystals precipitated were filtered, washed with acetone and dried over anhydrous phosphorus pentoxide to obtain 0.53 g of the desired product as the sodium salt. The resulting product was then purified with the following manner.

The resulting sodium salt was dissolved in water-methanol and then acidified with 6N-HCl while cooling. The crystals precipitated were filtered, washed with water-methanol and dried over anhydrous phosphorus pentoxide to obtain the purified desired product as the free acid form. The free acid thus obtained was dissolved in dimethylsulfoxide, and sodium 2-ethylhexanoate was then added to the solution. To the resulting solution was then dropwise added acetone. The crystals thus precipitated were filtered, washed with acetone and dried over anhydrous phosphorus pentoxide to obtain the desired product as the sodium salt.

EXAMPLE 2

Preparation of 3-[(1-Methyltetrazol-5-yl)thiomethyl]-7α-methoxy-7β-[D-2-(4-hydroxy-1,5-naphthyridine-3-carbonamido)-2-(p-hydroxyphenyl)acetamido]-3-cephem-4-carboxylic Acid

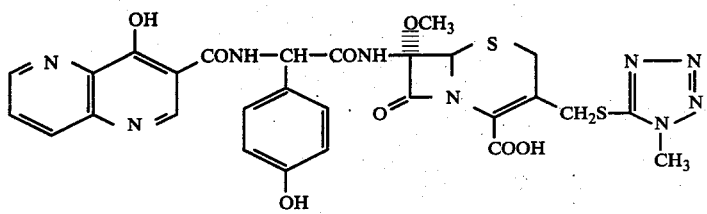

0.621 g of the trifluoroacetate salt of 3-[(1-methyltetrazol-5-yl)thiomethyl]-7α-methoxy-7β-[D-2-amino-2-(p-hydroxyphenyl)acetamido]-3-cephem-4-carboxylic acid was dissolved in 5 ml of dimethyl sulfoxide, and 0.303 g of triethylamine was then added to the solution. Then, 0.287 g of 4-hydroxy-1,5-naphthyridine-3-carboxylic acid N-hydroxysuccinimide ester was added to the solution, and the mixture was allowed to react for 1 hour at room temperature while stirring. After removal of any insoluble substances by filtration, 0.332 g of sodium 2-ethylhexanoate was added to the filtrate, and the resulting solution was added to 150 ml of acetone. The crystals precipitated were filtered, washed with acetone and dried over anhydrous phosphorus pentoxide to obtain 0.57 g of the desired product as the sodium salt. The resulting product was then purified in the same manner as was used in Example 1.

EXAMPLE 3

Preparation of 3-[(Triazol-5-yl)thiomethyl]-7α-methoxy-7β-[D-2-(4-hydroxy-1,5-naphthyridine-3-carbonamido)-2-(p-hydroxyphenyl)acetamido]-3-cephem-4-carboxylic Acid

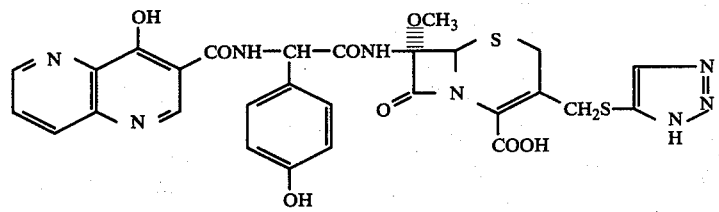

0.645 g of sodium 3-acetoxymethyl-7α-methoxy-7β-[D-2-(4-hydroxy-1,5-naphthyridine-3-carbonamido)-2-(p-hydroxyphenyl)acetamido]-3-cephem-4-carboxylate and 10 ml of a phosphate buffer (pH 6.4) were heated at a temperature of 50° C. in a nitrogen atmosphere, and a solution of 0.14 g of 5-mercaptotriazole in 5 ml of acetone was added dropwise thereto. 0.12 g of sodium bicarbonate was then added to the mixture and the resulting mixture was allowed to react for 17 hours at a temperature of 50° to 60° C. The acetone was then removed from the reaction mixture by distillation under reduced pressure, and the residue was adjusted to a pH of 2 with 3N hydrochloric acid. The crystals precipitated were filtered, washed successively with acetone and diethyl ether, and dried over anhydrous phosphorus pentoxide under reduced pressure to obtain 0.51 g of the desired product in the free carboxylic acid form. The acid thus obtained was converted into the sodium salt in a usual manner

EXAMPLE 4

Preparation of 3-Pyridiniummethyl-7α-methoxy-7β-[D-2-(4-hydroxy-1,5-naphthyridine-3-carbonamido)-2-phenylacetamido]-3-cephem-4-carboxylate

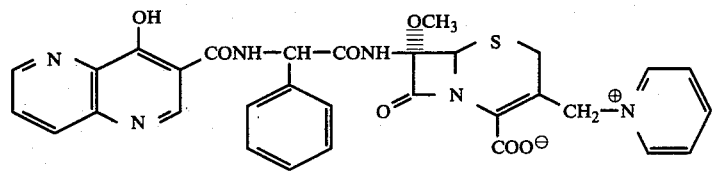

A solution of 0.63 g of sodium 3-acetoxymethyl-7α-methoxy-7β-[D-2-(4-hydroxy-1,5-naphthyridine-3-carbonamido)-2-phenylacetamido]-3-cephem-4-carboxylate, 1.9 g of potassium thiocyanate and 0.13 g of pyridine dissolved in 2 ml of water was adjusted to a pH of 6.5 with phosphoric acid and allowed to react for 15 hours at a temperature of 60° C. The reaction mixture was allowed to cool to room temperature (about 20°–30° C.) and diluted with water to a volume of 15 ml. The mixture was then washed 5 times with 5 ml portions of chloroform. The aqueous layer was cooled to 0° C. and adjusted to a pH of 2.0 with 6N hydrochloric acid. After stirring the mixture for about 1 hour, the precipitated crystals were separated by filtration and dried over anhydrous phosphorus pentoxide to obtain 0.48 g of the desired product as the hydrothiocyanate salt.

EXAMPLE 5

Preparation of
3-Carbamoyloxymethyl-7α-methoxy-7β-[D-2-(4-hydroxy-1,5-naphthyridine-3-carbonamido)-2-(p-hydroxyphenyl)acetamido]-3-cephem-4-carboxylic Acid

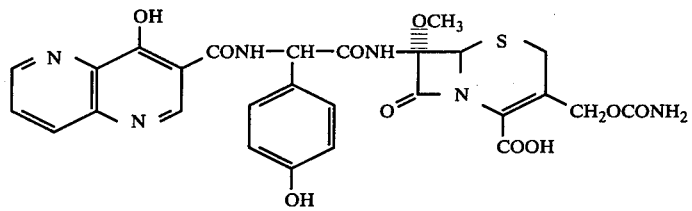

The titled compound was prepared in the same manner as described in Example 2 but using the trifluoroacetic acid salt of 3-carbamoyloxymethyl-7α-methoxy-7β-[D-2-amino-2-(p-hydroxyphenyl)acetamido]-3-cephem-4-carboxylic acid as a starting compound.

EXAMPLE 6

Preparation of
7α-Methoxy-7β-[2-(4-hydroxypyridine-3-carboxyamido)-2-phenyl]acetamido-cephalosporanic Acid A mixture of 0.27 g of 2-(3-hydroxypyridine-4-carboxyamido)-2-phenylacetic acid, 0.20 g of triethylamine and 20 ml of acetone were cooled to −20° C., and 0.22 g of ethyl chlorocarbonate was added thereto. The resulting mixture was then allowed to react for 1 hour while stirring and a solution of 0.47 g of 7α-methoxycephalosporanic acid benzhydryl ester dissolved in 10 ml of acetone was added to the reaction mixture. The mixture was then allowed to react while stirring for 1 hour at −20° C. to −10° C., for 1.5 hours at −10° C. to 0° C. and finally for 1 hour at 0° C. to 20° C. The reaction mixture was concentrated under reduced pressure, and the concentrate was purified by silica gel chromatography to obtain 0.3 g of 7α-methoxy-7β-[2-(3-hydroxypyridine-4-carboxyamido)-2-phenyl-]acetamidocephalosporanic acid benzhydryl ester.

The benzhydryl ester thus obtained was then stirred in ice-cooled trifluoroacetic acid for 30 minutes and then poured into diethyl ether to remove the benzhydryl ester moiety.

EXAMPLES 7 to 53

The following compounds were prepared in the same manner as described in Examples 1 to 6.

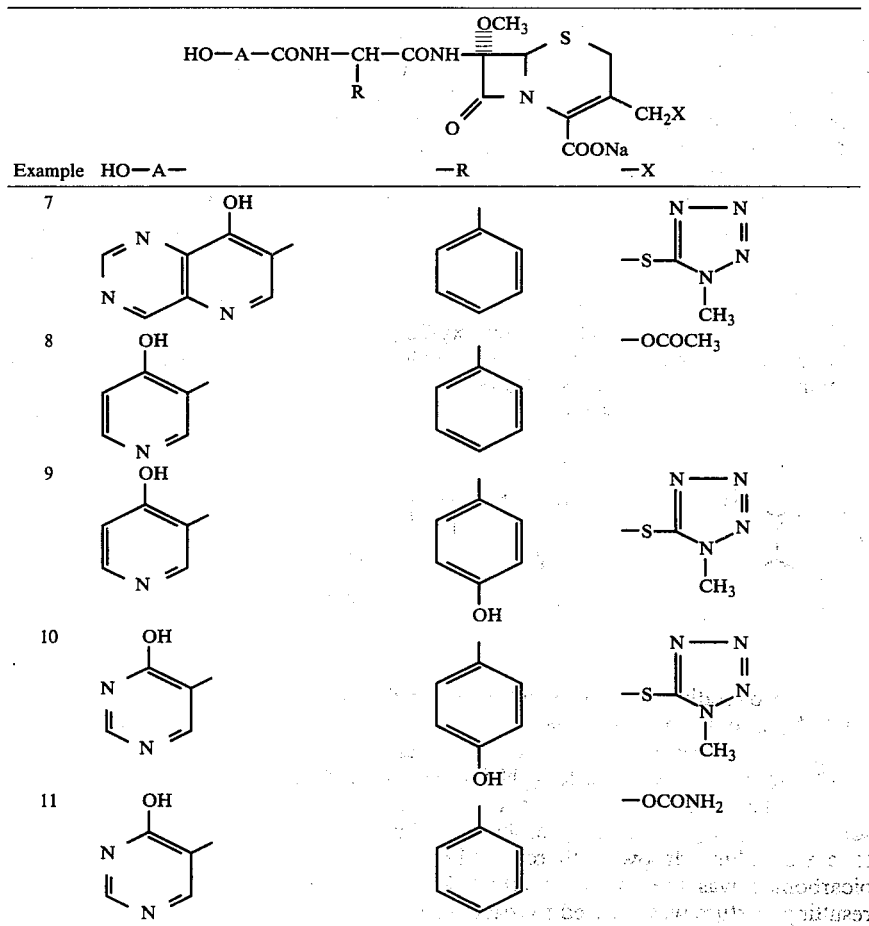

-continued

| Example | HO—A— | —R | —X |
|---|---|---|---|
| 12 | 3-hydroxy-4-methylpyridazin-yl | 4-hydroxyphenyl | -S-(1-methyl-1H-tetrazol-5-yl) |
| 13 | 3-hydroxy-4-methylpyridazin-yl | 4-hydroxyphenyl | -S-(5-methyl-1,3,4-thiadiazol-2-yl) |
| 14 | 3-hydroxy-4-methylpyridazin-yl | 4-hydroxyphenyl | -S-(2-thioxo-2,3-dihydro-1,3,4-thiadiazol-5-yl) |
| 15 | 4-hydroxy-3,7-dimethyl-1,8-naphthyridin-yl | 4-hydroxyphenyl | —OCOCH₃ |
| 16 | 4-hydroxy-3-methylpyridin-yl | phenyl | —N⁺(pyridinium) (—COO⁻ at 4-position) |
| 17 | 8-hydroxy-3-methoxy-7-methylpyrido[2,3-b]pyrazin-yl | 4-hydroxyphenyl | -S-(1-methyl-1H-tetrazol-5-yl) |
| 18 | 4-hydroxy-2-(methylthio)-6-methylpyrido[2,3-d]pyrimidin-yl | 4-hydroxyphenyl | —OCONH₂ |
| 19 | 4-hydroxy-2-(methylthio)-6-methylpyrido[2,3-d]pyrimidin-yl | 4-hydroxyphenyl | -S-(6-hydroxypyridazin-3-yl) |
| 20 | 4-hydroxy-2-(methylthio)-6-methyl-1,8-naphthyridin-yl | 3-chloro-4-hydroxyphenyl | -S-(5-hydroxymethyl-1,3,4-thiadiazol-2-yl) |

-continued
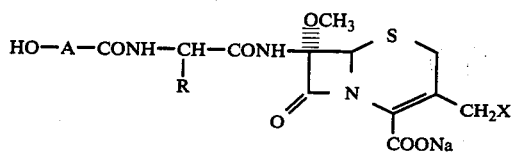
| Example | HO—A— | —R | —X |
|---|---|---|---|
| 21 | 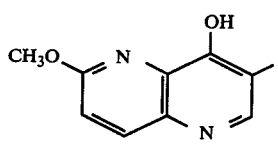 | 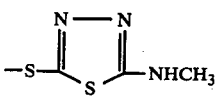 | 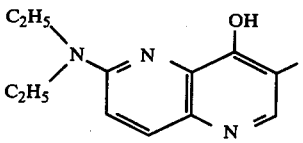 |
| 22 | 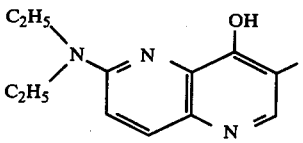 | 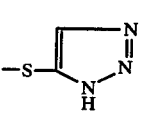 | 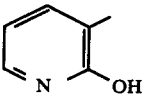 |
| 23 | 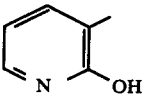 |  | —OCONH$_2$ |
| 24 | 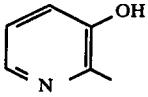 |  | 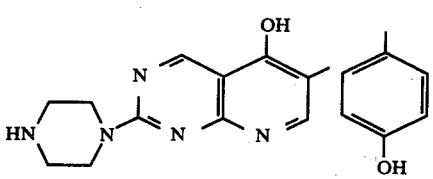 (—COO$^\ominus$ at 4-position) |
| 25 | 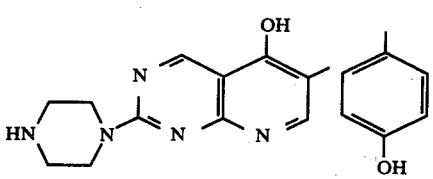 | 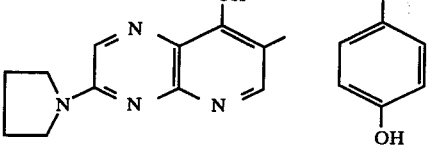 | —OCONH$_2$ |
| 26 | 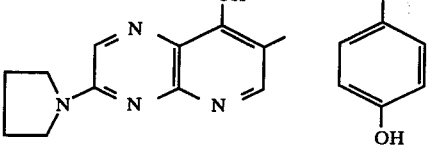 | 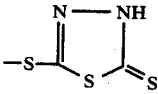 |  |
| 27 |  | 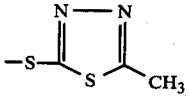 | 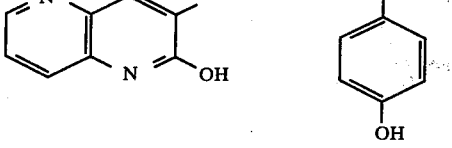 |
| 28 | 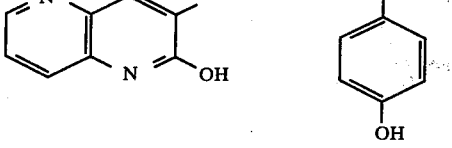 | 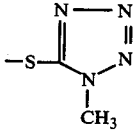 | 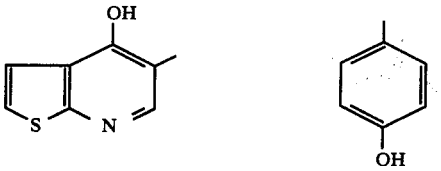 |
| 29 | 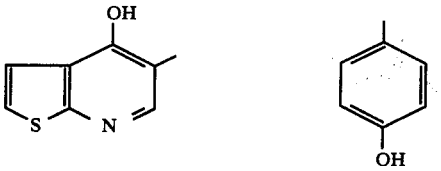 | 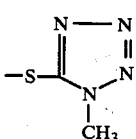 | 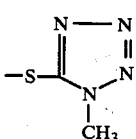 |

-continued
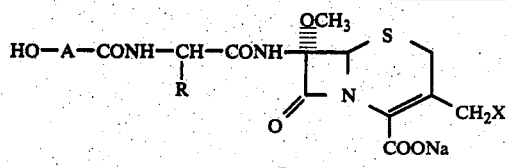
| Example | HO—A— | —R | —X |
|---|---|---|---|
| 30 | 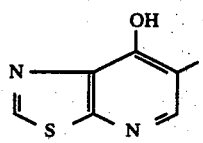 | 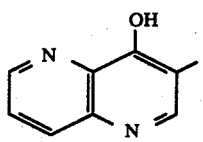 | —OCONH$_2$ |
| 31 | 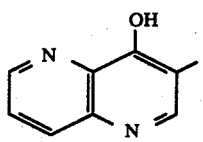 | 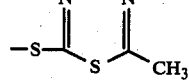 | 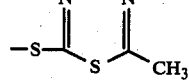 |
| 32 | 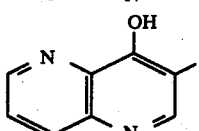 | 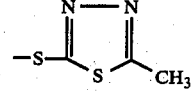 | 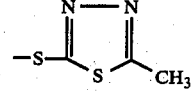 |
| 33 | 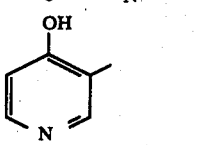 | 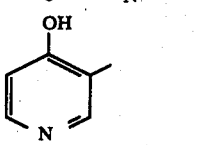 | —OCONH$_2$ |
| 34 | 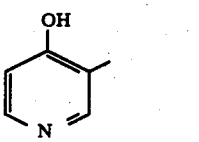 | 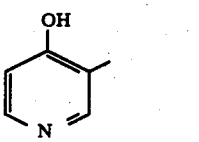 | 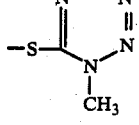 |
| 35 | 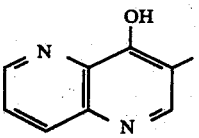 | 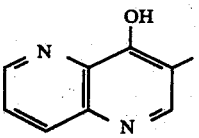 | 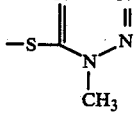 |
| 36 | 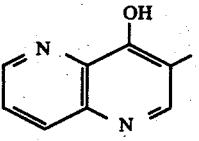 | 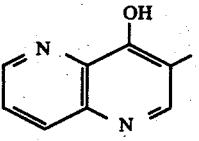 | —OCOCH$_3$ |
| 37 | 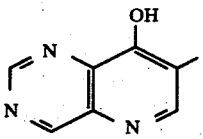 | 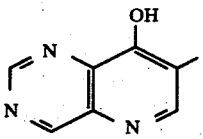 | 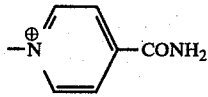 (—COO$^\ominus$ at 4-position) |
| 38 | 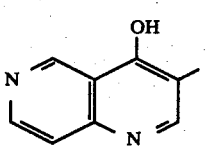 | 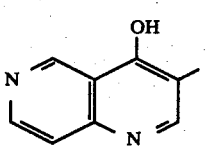 | 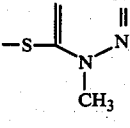 |
| 39 | 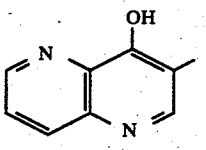 | 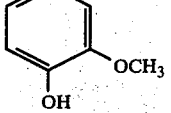 | —OCONH$_2$ |

-continued
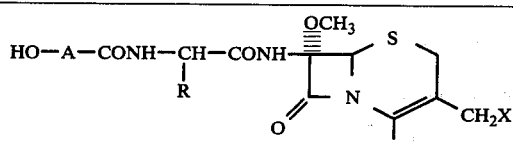
| Example | HO—A— | —R | —X |
|---|---|---|---|
| 40 | 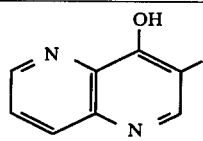 | 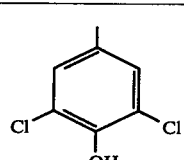 | 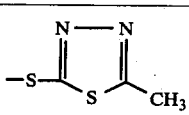 |
| 41 | 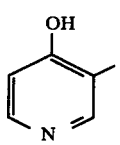 | 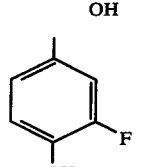 | 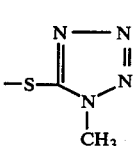 |
| 42 | 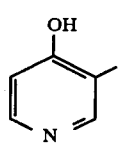 | 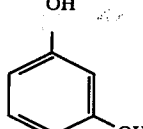 | 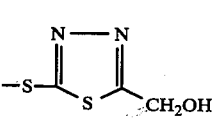 |
| 43 | 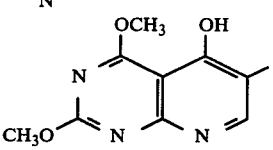 | 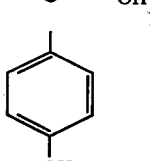 | 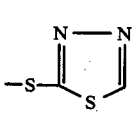 |
| 44 | 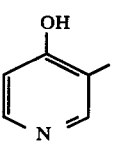 | 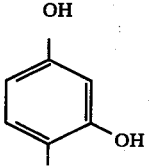 | —OCONH$_2$ |
| 45 | 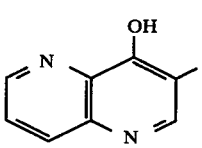 | 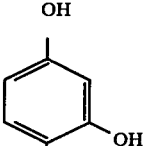 | 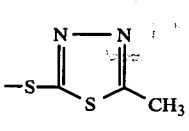 |
| 46 | 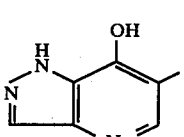 | 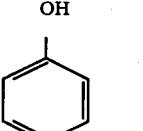 | 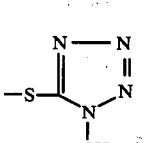 |
| 47 | 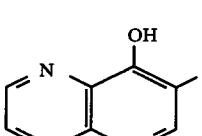 | 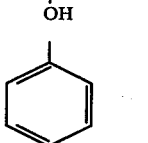 | 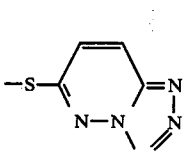 |
| 48 | 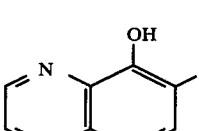 | 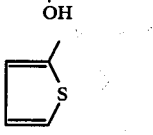 | —OCONH$_2$ |
| 49 | 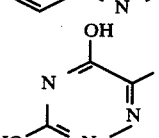 | 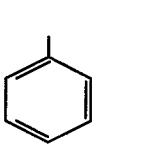 | —OCOCH$_3$ |

-continued

| Example | HO—A— | —R | —X |
|---|---|---|---|
| 50 | (OH, N, HO, N — triazine-like ring with methyl) | 4-hydroxyphenyl | -S-(1-methyl-tetrazol-5-yl) |
| 51 | (OH, N, CH3S, N — ring) | phenyl | —OCONH₂ |
| 52 | (OH, N, HO, N — ring) | 4-hydroxyphenyl | —OCONH₂ |
| 53 | (OH, N, HS, N — ring) | phenyl | -S-(5-methyl-1,3,4-thiadiazol-2-yl) |

REFERENCE EXAMPLE 1

Preparation of 3-Acetoxymethyl-7α-methoxy-7β-(2-amino-2-phenyl)-acetamido-3-cephem-4-carboxylic Acid Benzhydryl Ester Hydrochloride

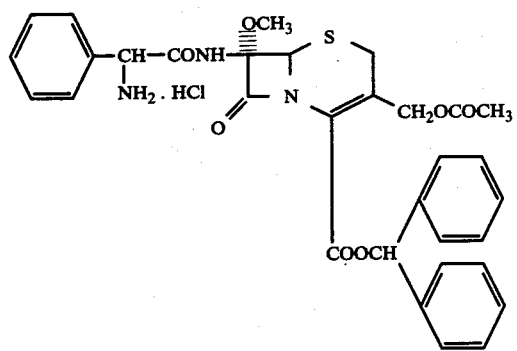

1.05 g of sodium bicarbonate was added to a suspension of 2.34 g of 3-acetoxymethyl-7α-methoxy-7β-amino-3-cephem-4-carboxylic acid benzhydryl ester, 1.28 g of D-phenylglycyl chloride hydrochloride and 20 ml of dichloromethane, and the mixture was stirred vigorously for 6 hours while cooling with ice. The reaction mixture was filtered to remove any insoluble materials. The insoluble materials were then washed with dichloromethane and the combined filtrate and washings were concentrated to dryness to obtain 2.8 g of the desired product.

REFERENCE EXAMPLE 2

Preparation of 3-Acetoxymethyl-7α-methoxy-7β-[(2-N-t-butoxycarbonylamino-2-phenyl)acetamido]-3-cephem-4-carboxylic Acid Benzhydryl Ester

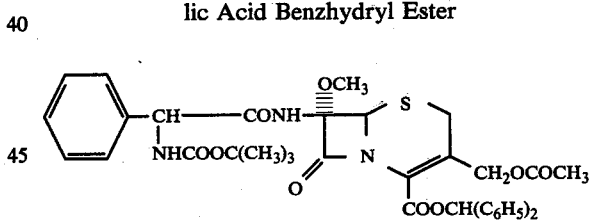

A solution of 2.52 g of D-α-t-butoxycarbonylaminophenylglycine, 1.01 g of triethylamine and 40 ml of tetrahydrofuran was cooled to −10° C. and 1.365 g of isobutyl chloroformate was added dropwise thereto followed by allowing the materials to react for 30 minutes. To the resulting reaction mixture was then added a solution of 4.68 g of 3-acetoxymethyl-7α-methoxy-7β-amino-3-cephem-4-carboxylic acid benzhydryl ester dissolved in tetrahydrofuran, and the mixture was allowed to react for 1.5 hours at −10° C. to −5° C. while stirring. The reaction mixture was then concentrated to dryness under reduced pressure, and the residue was dissolved in 50 ml of ethyl acetate. The ethyl acetate layer was washed with a cooled dilute aqueous solution of sodium bicarbonate, dried over anhydrous magnesium sulfate and concentrated under reduced pressure to obtain 5.2 g of the desired product.

REFERENCE EXAMPLE 3

Preparation of
3-Acetoxymethyl-7α-methoxy-7β-[(D-2-amino-2-phenyl)acetamido]-3-cephem-4-carboxylic Acid Trifluoroacetate

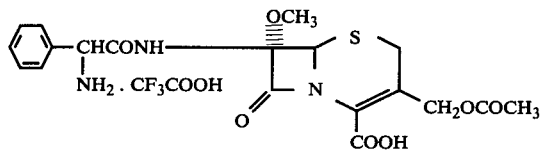

1.0 g of 3-acetoxymethyl-7α-methoxy-7β-[(2-N-t-butoxycarbonylamino-2-phenyl)acetamido]-3-cephem-4-carboxylic acid benzhydryl ester was added to a cooled solution of 5 ml of trifluoroacetic acid and 1 ml of anisole followed by stirring for 30 minutes. The reaction mixture was then poured into 200 ml of diethyl ether, and the precipitated crystals were filtered, washed with diethyl ether and dried over anhydrous phosphorus pentoxide under reduced pressure to obtain 0.45 g of the desired product.

REFERENCE EXAMPLE 4

Preparation of
3-Acetoxymethyl-7α-methoxy-7β-[2-(N-p-methoxybenzyloxycarbonylamino)-2-(p-hydroxyphenyl)acetamido]-3-cephem-4-carboxylic Acid Benzhydryl Ester

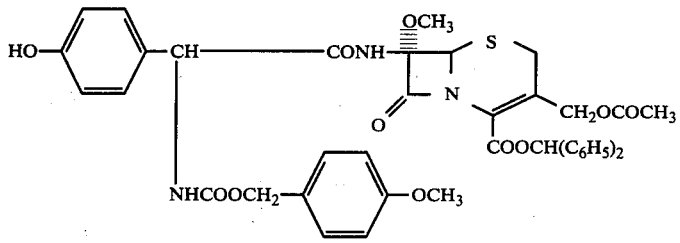

A solution of 3.31 g of D-α-p-methoxybenzyloxycarbonylamino-p-hydroxyphenylglycine, 1.01 g of N-methylmorpholine and 30 ml of acetonitrile was cooled to −10° C., and a solution of 1.36 g of isobutyl chloroformate in 5 ml of acetonitrile was added dropwise thereto followed by allowing the mixture to react for 40 minutes at −10° C. while stirring. A solution of 4.68 g of 3-acetoxymethyl-7α-methoxy-7β-amino-3-cephem-4-carboxylic acid benzhydryl ester in acetonitrile was added to the reaction mixture, and the resulting mixture was allowed to react for 1.5 hours at a temperature of −10° C. to −2° C. The solvent was then removed by distillation under reduced pressure and the residue was dissolved in dichloromethane. The dichloromethane layer was washed with a cooled dilute aqueous solution of sodium bicarbonate, dried over anhydrous magnesium sulfate and concentrated under reduced pressure to obtain 6.2 g of the desired product.

REFERENCE EXAMPLE 5

Preparation of
3-Acetoxymethyl-7α-methoxy-7β-[(D-2-amino-2-p-hydroxyphenyl)acetamido]-3-cephem-4-carboxylic Acid Trifluoroacetate

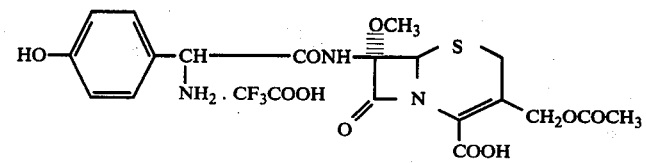

The above compound was prepared in the same manner as described in Reference Example 3.

In the same manner as described in Reference Examples 1 to 5, the following compounds were prepared.

3-[(1-Methyltetrazol-5-yl)thiomethyl]-7α-methoxy-7β-[(D-2-amino-2-phenyl)acetamido]-3-cephem-4-carboxylic acid benzhydryl ester hydrochloride;

3-Carbamoyloxymethyl-7α-methoxy-7β-[(D-2-amino-2-phenyl)acetamido]-3-cephem-4-carboxylic acid benzhydryl ester hydrochloride;

3-Carbamoyloxymethyl-7α-methoxy-7β-[(D-2-amino-2-phenyl)acetamido]-3-cephem-4-carboxylic acid trichloroethyl ester hydrochloride;

3-Carbamoyloxymethyl-7α-methoxy-7β-[(D-2-amino-2-p-hydroxyphenyl)acetamido]-3-cephem-4-carboxylic acid benzhydryl hydrochloride;

3-[(1-Methyltetrazol-5-yl)thiomethyl]-7α-methoxy-7β-[(D-2-amino-2-p-hydroxyphenyl)acetamido]-3-cephem-4-carboxylic acid benzhydryl hydrochloride;

3-[(5-Methyl-1,3,4-thiadiazol-2-yl)thiomethyl]-7α-methoxy-7β-[(D-2-amino-2-p-hydroxyphenyl)acetamido]-3-cephem-4-carboxylic acid p-nitrobenzyl ester hydrochloride;

3-Carbamoyloxymethyl-7α-methoxy-7β-[D-2-amino-2-(2-thienyl)acetamido]-3-cephem-4-carboxylic acid benzhydryl ester hydrochloride;

3-[(1-Methyltetrazol-5-yl)thiomethyl]-7α-methoxy-7β-[(2-amino-2-furyl)acetamido]-3-cephem-4-carboxylic acid trichloroethyl ester hydrochloride;

3-Acetoxymethyl-7α-methoxy-7β-[(D-2-amino-2-cyclohexadienyl)acetamido]-3-cephem-4-carboxylic acid benzhydryl ester hydrochloride;

3-[(1-Methyltetrazol-5-yl)thiomethyl]-7α-methoxy-7β-[(D-2-amino-2-phenyl)acetamido]-3-cephem-4-carboxylic acid trifluoroacetate;

3-[(1-Methyltetrazol-5-yl)thiomethyl]-7α-methoxy-7β-[(D-2-amino-2-p-hydroxyphenyl)acetamido]-3-cephem-4-carboxylic acid trifluoroacetate;

3-Carbamoyloxymethyl-7α-methoxy-7β-[(D-2-amino-2-p-hydroxyphenyl)acetamido]-3-cephem-4-carboxylic acid trifluoroacetate;

3-Acetoxymethyl-7α-methoxy-7β-[D-2-p-hydroxy-m-chlorophenyl)acetamido]-3-cephem-4-carboxylic acid trifluoroacetate;

3-[(Triazol-5-yl)thiomethyl]-7α-methoxy-7β-[(D-2-amino-2-p-hydroxyphenyl)acetamido]-3-cephem-4-carboxylic acid trifluoroacetate;

3-Acetoxymethyl-7α-methoxy-7β-[D-2-amino-2-(2-thienyl)acetamido]-3-cephem-4-carboxylic acid trifluoroacetate; and 3-Acetoxymethyl-7α-methoxy-7β-[D-2-amino-2-(2-furyl)acetamido]-3-cephem-4-carboxylic acid trifluoroacetate.

The antimicrobial activities of the compounds prepared in the previous Examples were determined in a usual manner and the minimum inhibitory concentrations (in terms of μg/ml) are set forth in the Table below.

TABLE

Minimum Inhibitory Concentration (μg/ml)

| Compounds (Example No.) | Escherichia coli NIHJ | Proteus vulgaris HX 19 | Pseudomonas aeruginosa IID 5142 | Serratia No. 115 | Enterobacter aerogenes No. 101 |
|---|---|---|---|---|---|
| 1 | 3.13 | 0.39 | 1.56 | 50 | 6.25 |
| 2 | 0.78 | 0.2 | 1.56 | 3.13 | 3.13 |
| 3 | 3.13 | 0.78 | 3.13 | 25 | 6.25 |
| 4 | 3.13 | 0.78 | 6.25 | 25 | 12.5 |
| 5 | 3.13 | 0.39 | 3.13 | 50 | 6.25 |
| 7 | 6.25 | 0.78 | 6.25 | 12.5 | 6.25 |
| 8 | 12.5 | 0.39 | 6.25 | 100 | 25 |
| 9 | 12.5 | 0.39 | 6.25 | 50 | 12.5 |
| 10 | 12.5 | 0.39 | 12.5 | 50 | 12.5 |
| 11 | 12.5 | 0.78 | 12.5 | 100 | 50 |
| 12 | 12.5 | 0.78 | 25 | 100 | 25 |
| 13 | 12.5 | 0.78 | 25 | 100 | 25 |
| 14 | 12.5 | 1.56 | 25 | 100 | 25 |
| 15 | 12.5 | 1.56 | 12.5 | 100 | 50 |
| 16 | 12.5 | 1.56 | 6.25 | 50 | 25 |
| 17 | 3.13 | 0.2 | 3.13 | 6.25 | 6.25 |
| 18 | 12.5 | 0.78 | 6.25 | 50 | 12.5 |
| 19 | 6.25 | 0.78 | 3.13 | 25 | 12.5 |
| 20 | 3.13 | 0.39 | 3.13 | 6.25 | 6.25 |
| 21 | 1.56 | 0.39 | 3.13 | 12.5 | 6.25 |
| 22 | 3.13 | 0.39 | 3.13 | 25 | 6.25 |
| 23 | 12.5 | 0.78 | 12.5 | 100 | 50 |
| 24 | 12.5 | 0.78 | 12.5 | 50 | 25 |
| 25 | 12.5 | 0.78 | 6.25 | 50 | 25 |
| 26 | 6.25 | 0.39 | 6.25 | 12.5 | 12.5 |
| 27 | 25 | 1.56 | 25 | 50 | 50 |
| 28 | 1.56 | 0.39 | 3.13 | 6.25 | 6.25 |
| 29 | 12.5 | 0.78 | 6.25 | 12.5 | 12.5 |
| 30 | 6.25 | 0.39 | 6.25 | 12.5 | 12.5 |
| 31 | 3.13 | 0.39 | 3.13 | 25 | 6.25 |
| 32 | 3.13 | 0.39 | 3.13 | 25 | 6.25 |
| 33 | 12.5 | 0.39 | 12.5 | 100 | 50 |
| 34 | 12.5 | 0.39 | 6.25 | 50 | 12.5 |
| 35 | 1.56 | 0.39 | 3.13 | 6.25 | 3.13 |
| 36 | 3.13 | 0.39 | 3.13 | 50 | 12.5 |
| 37 | 6.25 | 0.78 | 12.5 | 50 | 6.25 |
| 38 | 12.5 | 0.78 | 12.5 | 25 | 12.5 |
| 39 | 3.13 | 0.78 | 3.13 | 50 | 12.5 |
| 40 | 6.25 | 0.78 | 3.13 | 12.5 | 6.25 |
| 41 | 12.5 | 0.39 | 6.25 | 50 | 12.5 |
| 42 | 12.5 | 0.78 | 12.5 | 50 | 25 |
| 43 | 12.5 | 1.56 | 12.5 | 50 | 25 |
| 44 | 12.5 | 0.78 | 12.5 | 100 | 50 |
| 45 | 3.13 | 0.78 | 6.25 | 12.5 | 12.5 |
| 46 | 1.56 | 0.39 | 6.25 | 6.25 | 6.25 |
| 47 | 3.13 | 0.39 | 6.25 | 12.5 | 6.25 |
| 48 | 3.13 | 0.39 | 3.13 | 100 | 6.25 |
| 49 | 25 | 1.56 | 25 | 100 | 50 |
| 50 | 12.5 | 1.56 | 12.5 | 50 | 25 |
| 51 | 25 | 1.56 | 25 | 100 | 50 |
| 52 | 25 | 1.56 | 25 | 100 | 50 |
| 53 | 25 | 1.56 | 25 | 100 | 50 |

While the invention has been described in detail and with reference to specific embodiments thereof, it will be apparent to one skilled in the art that various changes and modifications can be made therein without departing from the spirit and scope thereof.

What is claimed is:

1. A cephalosporin of the formula (I):

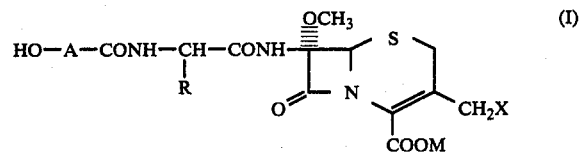

wherein A is a heteroaromatic ring selected from the group consisting of quinoline, isoquinoline, cinnoline, naphthyridine, quinoxaline, pyrazolopyridine, pyridopyrazine, thiazolopyrimidine, pyridopyrimidine, pyrimidinopyridazine, thienopyridine, thiazolopyridine, pyridine, pyrimidine, pyridazine, triazine, and pyrazine, each of which may be substituted with one or two substituents selected from the group consisting of halogen, $(C_1-C_4)$alkyl, $(C_1-C_4)$alkoxy, $(C_2-C_5)$alkanoyl, $(C_2-C_5)$alkoxycarbonyl, $(C_1-C_4)$alkylthio, mercapto, hydroxy, $(C_2-C_5)$alkoxymethyl, cyano, nitro, $(C_1-C_4)$alkylsulfonyl, phenylsulfonyl, sulfamoyl, carbamoyl, phenyloxycarbonylamino, acetoacetylamino, $(C_1-C_4)$alkylamino, di-$(C_1-C_4)$alkylamino, halo-$(C_1-C_4)$alkyl, $(C_2-C_5)$alkenyl, phenyl, $(C_3-C_6)$cycloalkyl, $(C_4-C_6)$cycloalkylene, piperazino, piperidino, pyrrolidino, and morpholino; R is a phenyl group which may be unsubstituted or substituted with up to three chemically compatible substituents selected from the group consisting of nitro, di-$(C_1-C_4)$alkylamino, $(C_2-C_5)$alkanoylamino, $(C_1-C_4)$alkylsulfonamino, amino hydroxy, $(C_2-C_5)$alkanoyloxy, $(C_1-C_4)$alkyl, $(C_1-C_4)$alkoxy, chloro, bromo, fluoro, iodo, trifluoromethyl, hydroxymethyl, ureido or sulfamyl; a thienyl group; a furyl group; a cyclohexadienyl group or a cyclohexenyl group; X is -S-Het in which Het is tetrazolyl, thiadiazolyl, triazolyl, oxadiazolyl, pyridazinyl, tetrazolo-[4,5-b]pyridazinyl, pyridazino[3,2-c]-S-triazolyl or pyridazino-[2,1-c]-S-triazolyl, each of which may be unsubstituted or substituted with 1 or 2 substituents selected from the group consisting of $(C_1-C_4)$alkyl, $(C_1-C_4)$alkoxy, hydroxy, mercapto, hydroxymethyl, aminomethyl and methylamino; and M is a hydrogen atom or a biologically active carbonyl-protecting group, and the non-toxic pharmaceutically acceptable salts thereof.

2. The compound of claim 1, wherein R is a phenyl group which is unsubstituted or substituted with up to three chemically compatible substituents selected from the group consisting of hydroxy, chlorine, fluorine, or methoxy.

3. The compound of claim 1, wherein Het is 1-methyltetrazol-5-yl, 2-methyl-1,3,4-thiadiazol-5-yl, 1,2,3-triazol-5-yl, 1,2,4-triazol-3-yl, tetrazol-5-yl, 2-methyl-tetrazol-5-yl, 2-mercapto-1,3,4-thiadiazol-5-yl, 2-hydroxymethyl-1,3,4-oxadiazol-5-yl, 2-hydroxymethyl-1,3,4-thiadiazol-5-yl, 2-aminomethyl-1,3,4-thiadiazol-5-yl, 3-hydroxypyridazin-6-yl, 1,3,4-thiadiazol-5-yl, 2-methylamino-1,3,4-thiadiazol-5-yl, 2-oxo-1,3,4-thiadiazol-5-yl, 1-ethyltetrazol-5-yl, 1-phenyltetrazol-5-yl, tetrazolo[4,5-b]pyridazin-6-yl, 3-hydroxypyridazino[3,2-c]-S-triazol-6-yl, pyridazino[2,1-c]-S-triazol-3-yl, or pyrido[2,1-c]-S-triazol-3-yl.

4. A cephalosporin of the formula (I):

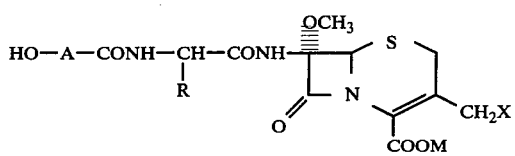

wherein R is phenyl; X is -S-Het in which Het is tetrazole or thiadiazole, each of which may be unsubstituted or substituted with ($C_1$ - $C_4$) alkyl; A is pyridopyrimidine which may be unsubstituted or substituted with ($C_1$ - $C_4$) alkylmercapto, or triazine substituted with hydroxy, and M is hydrogen.

5. A cephalosporin of the formula (I):

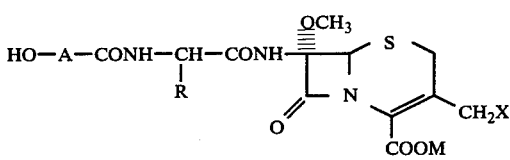

wherein R is

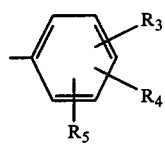

in which $R_3$, $R_4$ and $R_5$ each is hydrogen, hydroxy, ($C_1$ - $C_4$)alkoxy, chlorine or fluorine; X is -S-Het wherein Het is tetrazole, triazole, thiadiazole, pyridazine or tetrazolopyridazine, each of which may be unsubstituted or substituted with one substituent selected from the group consisting of ($C_1$ - $C_4$)alkyl, hydroxy, hydroxymethyl, mercapto, methylamino and aminomethyl; A is naphthyridine, pyridopyrazine, pyrazolopyridine, pyridopyrimidine, thienopyridine, pyridine, pyrimidine, pyridazine, pyrazine or triazine, each of which may be unsubstituted or substituted with one substituent selected from the group consisting of ($C_1$ - $C_4$)alkyl, ($C_1$ - $C_4$)alkoxy, ($C_1$ - $C_4$)alkylmercapto, di-($C_1$ - $C_4$)alkylamino and hydroxy; and M is hydrogen.

6. A cephalosporin of the formula (I):

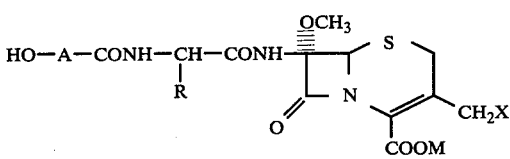

wherein R is thienyl; X is -S-Het wherein Het is tetrazole which may be unsubstituted or substituted with ($C_1$ - $C_4$)alkyl; A is pyridine which may be unsubstituted or substituted with ($C_1$ - $C_4$)alkyl or hydroxy; and M is hydrogen.

7. A cephalosporin of the formula (I):

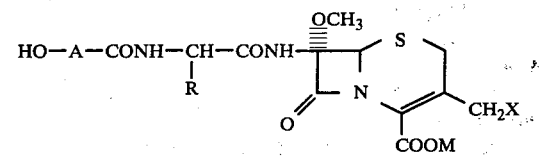

wherein R is cyclohexadienyl; X is -S-Het wherein Het is thiadiazole which may be unsubstituted or substituted with ($C_1$ - $C_4$)alkyl; A is naphthyridine which may be unsubstituted or substituted with one substituent selected from the group consisting of ($C_1$ - $C_4$)alkyl, ($C_1$ - $C_4$)alkylmercapto and di-($C_1$ - $C_4$)alkylamino; and M is hydrogen.

8. A cephalosporin of the formula (I):

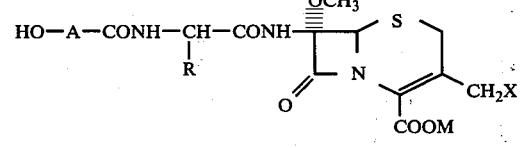

wherein R is furyl; X is -S-Het wherein Het is tetrazole which may be unsubstituted or substituted with ($C_1$ - $C_4$)alkyl; A is naphthyridine which may be unsubstituted or substituted with one substituent selected from the group consisting of ($C_1$ - $C_4$)alkyl, ($C_1$ - $C_4$)alkoxy, ($C_1$ - $C_4$)alkylmercapto and di-($C_1$ - $C_4$)alkylamino; and M is hydrogen.

9. A cephalosporin of the formula (I):

wherein R is phenyl; X is -S-Het wherein Het is tetrazole or thiadiazole, each of which may be unsubstituted or substituted with ($C_1$ - $C_4$)alkyl; A is pyridine or naphthyridine, each of which may be unsubstituted or substituted with one substituent selected from the group consisting of ($C_1$ - $C_4$)alkyl, ($C_1$ - $C_4$)alkoxy, ($C_1$ - $C_4$)alkylmercapto, di-($C_1$ - $C_4$)alkylamino and hydroxy; and M is hydrogen.

10. A cephalosporin of the formula (I):

wherein R is thienyl; X is -S-Het wherein Het is tetrazole or thiadiazole, each of which may be unsubstituted or substituted with ($C_1$ - $C_4$)alkyl; A is naphthyridine which may be unsubstituted or substituted with one substituent selected from the group consisting of ($C_1$ - $C_4$)alkyl, ($C_1$ - $C_4$)alkoxy, ($C_1$ - $C_4$)alkylmercapto and di-($C_1$ - $C_4$)alkylamino; and M is hydrogen.

11. A cephalosporin of the formula (I):

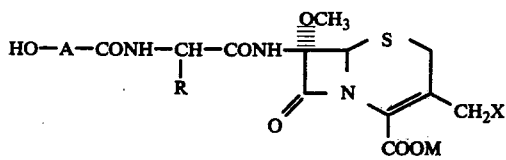

wherein R is cyclohexadienyl; X is -S-Het wherein Het is tetrazole or thiadiazole, each of which may be unsubstituted or substituted with ($C_1$ - $C_4$)alkyl; A is pyridine which may be unsubstituted or substituted with ($C_1$ - $C_4$)alkyl or hydroxy; and M is hydrogen.

12. A cephalosporin of the formula (I):

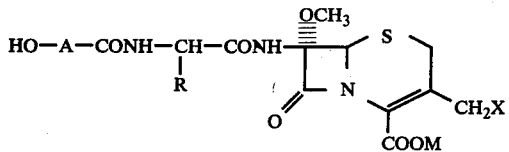

wherein R is furyl; X is -S-Het wherein Het is tetrazole or thiadiazole, each of which may be unsubstituted or substituted with ($C_1$ - $C_4$)alkyl; A is pyridine which may be unsubstituted or substituted with ($C_1$ - $C_4$)alkyl or hydroxy; and M is hydrogen.

13. An antimicrobial composition which comprises an antimicrobially effective amount of at least one compound of the formula (I) of claim 1 as an active ingredient and a pharmaceutically acceptable carrier or diluent.

14. A method of treating or preventing infectious diseases caused by Gram-positive or Gram-negative bacteria in an animal which comprises administering an antimicrobially effective amount of at least one compound of the formula (I) of claim 1 to said animal.

* * * * *